United States Patent [19]

Barrault et al.

[11] 4,143,052

[45] Mar. 6, 1979

[54] PROCESS FOR PREPARING THIOPHENES

[75] Inventors: Joél Barrault, Liguge; Michel Guisnet, Poitiers; Jacques Lucien, Le Mesnil Esnard; Raymond Maurel, Jaunay Clan, all of France

[73] Assignee: Societe Nationale Elf Aquitaine (Production), Paris, France

[21] Appl. No.: 860,828

[22] Filed: Dec. 15, 1977

[30] Foreign Application Priority Data

Dec. 23, 1976 [FR] France .................................. 76 38842

[51] Int. Cl.² ............................................. C07D 333/10
[52] U.S. Cl. ........................... 260/329 R; 260/330.5; 260/332.8
[58] Field of Search ............... 260/332.8, 329 R, 330.5

[56] References Cited

U.S. PATENT DOCUMENTS

| 2,558,507 | 6/1951 | Appleby et al. | 260/332.8 |
| 3,822,289 | 7/1974 | Clark et al. | 260/332.8 |
| 3,939,179 | 2/1976 | Bell et al. | 260/332.8 |

OTHER PUBLICATIONS

Hartough, "Thiophene and Its Derivatives," pp. 48–55 (1952).
Chemical Abstracts, vol. 71, column 60, 610(z), (1969).
Chemical Abstracts, vol. 69 column 66,858(s), (1968).
Chemical Abstracts, vol. 51 column 1,039(f).

*Primary Examiner*—Gerald A. Schwartz
*Attorney, Agent, or Firm*—Ostrolenk, Faber, Gerb & Soffen

[57] ABSTRACT

Preparation of a thiophene by the action of $H_2S$ on an organic substance containing oxygen or sulphur.

The substance which is used is an unsaturated carbonyl or thiocarbonyl compound, particularly an aldehyde, thioaldehyde, ketone or thioketone. The reaction preferably takes place between 250° and 500° C. on a catalyst of the alumina type containing an alkali or alkaline earth oxide.

The process permits the unsubstituted or substituted thiophene to be obtained with high yields and high degrees of selectivity, exceeding 70%.

15 Claims, No Drawings

PROCESS FOR PREPARING THIOPHENES

The present invention is concerned with the production of thiophenes.

Since the thiophenes are products which are of industrial interest, several processes have been proposed for the preparation thereof. In particular, the reaction of hydrogen sulphide under heat, in the presence of catalysts, on various hydrocarbons, such as acetylene, butane, butenes, butadiene, have been used. The action of sulphur or of $SO_2$ on butene has also been proposed. Furthermore, experiments have been carried out with methods of dehydrocyclisation of sulphides, dehydrogenation of thioorganic compounds and of cyclisation of $\gamma$-diketones or diacids. However, none of these prior processes has permitted thiophene to be obtained economically and the yields of the desired products rarely exceed 50%. The only method which leads to the unsubstituted thiophene with good selectivity and yields, which may exceed 90%, is the reaction of $H_2S$ on furan; nevertheless, the yield falls to about 50% as soon as an attempt is made to produce a substituted thiophene, for example, 2-methyl-thiophene; on the other hand, the furans are rather involved products, and the expense in obtaining them seriously complicate the manufacture of the thiophenes.

The present invention proposes a new process which makes possible the economic production of unsubstituted thiophene and its derivatives, especially alkyl thiophenes, with good yields and starting from readily available initial materials.

The new process according to the invention consists in causing the action of hydrogen sulphide on an unsaturated carbonyl or thiocarbonyl compound, such as aldehyde, thioaldehyde, ketone or thioketone which carries a double bond.

The reaction on which the process according to the invention is based may be illustrated by the equation:

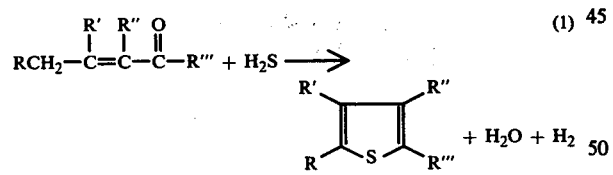

in which each of the symbols R, R', R" and R''', which are like or different, represents a hydrogen atom or an alkyl.

The starting compound may be selected, for example, from substances such as crotonaldehyde, mesityl oxide, methylethyl-acrolein or the corresponding thio derivatives, which are transiently formed in the reaction (1). Industrially, it is more practical to make use of the aforementioned oxygenated compounds. It is to be noted that the carbonyl or thiocarbonyl compounds which are used according to the invention are generally speaking, initial materials which are easily available, since they may be readily obtained by crotonisation of conventional carbonyl compounds, as for example ethanal, propanal, acetone, etc.

As indicated by the equation (1), the reaction in accordance with the invention comprises simultaneously a condensation, a cyclisation and a dehydrogenation; so that these three transformations proceed in a suitable manner, it is expedient to operate at a sufficiently high temperature on a suitable catalyst. Furthermore, in accordance with one of the features of the present invention, the operation takes place at a temperature higher than 200°C., particularly between 250° and 500° C. and preferably between 300° and 400° C. The catalyst which is particularly suitable is alumina, especially that which is known under the term "alumina A"; this is a highly microporous alumina which is not very crystallised and in the $\gamma$-form. This catalyst may be further improved by adding a certain proportion of basic substances, mainly oxides or sulphides of sodium or potassium.

Very good results are also obtained with the $\gamma$-alumina which is known under the commercial name "GBS". The activity of the catalyst is essentially improved by adding about 0.5 to 15% by weight of $K_2O$, $Na_2O$ or an equivalent quantity of corresponding sulphide.

The contact time between the reaction medium and the catalyst, for a given conversion, depends on the temperature. Thus, for a conversion which is practically complete, at 400° C., this contact time is about 3.65 seconds; it is 9.1 seconds at 370°. At 350° C., it is necessary to have a time of 13.7 seconds to achieve a conversion of 87%.

Although equation (1) indicates that 1 mole of $H_2S$ is required for one of the carbonyl or thiocarbonyl compounds, the best results are obtained with an excess of hydrogen sulphide, namely, with more than 2 moles of $H_2S$ per mole of carbonyl or thiocarbonyl and preferably up to 5 or more moles.

The reaction according to the invention takes place in gaseous phase under atmospheric pressure or under a higher pressure, for example, up to 10 bars.

The invention is illustrated without and limitation by the following examples.

EXAMPLES 1 TO 6

Preparation of thiophene from crotonaldehyde and $H_2S$. The reaction which takes place corresponds to the equation:

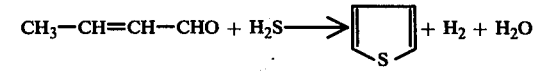

Different catalysts are tested at 400° C. with a molar ratio between $H_2S$ and crotonaldehyde of 5, with a contact time of one second. The liquid carbonyl derivative is introduced continuously into a preheating reactor, at the same time as the expanded hydrogen sulphide. After passing into a catalytic reactor the effluents are condensed, collected and subjected to the separation of the formed products. The following table indicates, in respect of the different catalysts which have been tested, the activities of these catalysts after functioning for 30 hours, that is to say, the productions in moles of thiophene per hour, per kg of catalyst.

| Ex. | Catalyst | Total activity | Selectivity % of | | | |
|---|---|---|---|---|---|---|
| | | | Thiophene | Light products | Butanal | Heavy products |
| 1 | silica-alumina (13.5% $Al_2O_3$) | 1.7 | 25.0 | 75.0 | — | — |
| 2 | alumina A | 4.3 | 77.0 | 12.0 | 2.5 | 8.5 |
| 3 | alumina A + 3.7% $WO_3$ | 4.6 | 55.0 | 36.0 | — | 9.0 |
| 4 | alumina A + 3.2% $K_2O$ | 8.4 | 74.5 | 7.0 | 1.5 | 17.0 |
| 5 | alumina A + 6.8 $K_2WO_4$ | 4.0 | 67.0 | 26.5 | — | 6.5 |
| 6 | $Al_2O_3$ + 20% chromium oxide | 5.2 | 74.5 | 13.5 | 3.5 | 8.5 |

It is seen that the addition of $K_2O$ (example 4) doubles the activity of the alumina A, while leading to an excellent selectivity with respect to thiophene.

EXAMPLES 7 TO 12

The same operating procedure as that of Examples 1 to 6 is applied to a series of catalysts which are formed by alumina A to which different proportions of potash are added.

The results are set out in the following table, in which the third vertical column indicates the specific surface of the catalyst in $m^2/g$.

| Ex. | % $K_2O$ added to alumina A | Area $m^2/g$ | Activity | Selectivities % of | | | |
|---|---|---|---|---|---|---|---|
| | | | | Thiophene | Light products | butanal | heavy products |
| 7 | 0 | 335 | 4.3 | 77.0 | 2.0 | 2.5 | 8.5 |
| 8 | 3.2% | 265 | 8,4 | 74.5 | 7.0 | 1.5 | 17.0 |
| 9 | 7.7% | 203 | 14.6 | 76.0 | 6.0 | 3.5 | 14.5 |
| 10 | 10.5% | 125 | 13.4 | 75.0 | 4.0 | 3.0 | 18.0 |
| 11 | 15.3% | 67 | 4.2 | 81.0 | 14.0 | 1.5 | 3.5 |
| 12 | 21.5% | 12 | Σ | — | — | — | — |

It is shown therefrom that the optimum as regards the potash content is between 3.2 and about 13%; with 15.3% of $K_2O$, the activity starts to fall relatively to that of the alumina A by itself, although the selectivity as regards thiophene is better. The maximum of the activity, combined with a very good selectivity (76%) is situated between 7 and 10%, and particularly at about 7.7% of $K_2O$.

For each of the catalysts as indicated above, the activity has been established, that is to say, the production in moles of thiophene per hour and per kg of catalyst, for variable operational periods. These investigations led to the following results:

| | | Production after | | | |
|---|---|---|---|---|---|
| Ex. | % $K_2O$ | 10 hours | 20 hours | 30 hours | 40 hours |
| 7 | 0 | 11.4 | 6.0 | 3.3 | 2.6 |
| 8 | 3.2 | 14.7 | 9.2 | 6.3 | 5.0 |
| 9 | 7.7 | 14.0 | 12.2 | 11.1 | 10.7 |
| 10 | 10.5 | 11.6 | 10.4 | 10.1 | 9.7 |
| 11 | 15.3 | 5.85 | 3.80 | 3.45 | 3.20 |

It is possible to establish that, with contents of $K_2O$ of 7.7 to 10.5% in the alumina A, the deactivation of the catalyst, i.e. the decrease in production, is much less than that for alumina by itself or for the alumina which contains 15.3% of potash. This improvement is considerable, since the activity of the alumina by itself (example 7) falls from 11.4 to 2.6 in 40 hours, i.e. by 77.2% of its initial value; on the other hand, with 10.5% of $K_2O$ (example 10) the decrease is only from 11.6 to 9.7, i.e. barely 16.5%.

EXAMPLES 13 TO 16

Addition of different bases to the alumina A.

The tests are carried out under the same conditions as regards temperature and molar ratio as those in the preceding examples.

The catalysts of Examples 13 and 14 are prepared by impregnation of the alumina with respectively solutions of potassium hydroxide and sodium hydroxide; the catalysts of Examples 15 and 16 are obtained by impregnation with the respective acetates of magnesium and calcium.

The quantities of potash (potassium oxide) sodium oxide, magnesium oxide and calcium oxide thus incorporated into the alumina A are equivalent to one another from a molar respect.

The activities and selectivities after operating for 30 hours are indicated in the following table.

| Ex. | Added base | Area $m^2/g$ | Activity | Selectivities % of | | | |
|---|---|---|---|---|---|---|---|
| | | | | Thiophene | Selectivities light products | % of butanal | heavy products |
| 13 | 7.7% $K_2O$ | 203 | 24.6 | 76.0 | 6.0 | 3.5 | 14.5 |
| 14 | 4.9% $Na_2O$ | 185 | 17.2 | 70.0 | 8.5 | 2.0 | 19.5 |
| 15 | 3.5% MgO | 235 | 3.9 | 71.0 | 23.0 | — | 6.0 |
| 16 | 4.5% CaO | 230 | 3.2 | 67.0 | 25.0 | — | 8.0 |

These results show that the sodium oxide has an effect similar to that of the potassium oxide; on the other hand, the calcium oxide and magnesium oxide lead to a rapid deactivation of the catalyst and the activities, after operating for 30 hours, are close to those of the initial alumina.

EXAMPLES 17 TO 21

Thiophenes were prepared, using the operating procedure of the foregoing examples, with the use of certain of the typical aluminas obtainable commercially.

Given below are the commercial names and the characteristics of the aluminas which were tested.

| Alumina | Area m²/g | Mean radius of pores Å | Various comments |
|---|---|---|---|
| Alumina A | 335 | very microporous 10-20 | not very crystallised in γ-form |
| SAP 350 | 290 | very microporous 13-22 | not very crystallised in γ-form |
| BAE 52A | 250 | 20 | alumina η |
| GBS | 190-200 | ~ 90 | alumina γ |
| SCS 9 | 24 | ~ 3000 | alumina α |

To each of these aluminas were added 7 to 8% of $K_2O$. The following table gives the results as regards preparation of thiophene.

| Ex. | Catalysts with 7 to 8% $K_2O$ | Activity | Selectivities % of | | | |
|---|---|---|---|---|---|---|
| | | | Thiophene | light products | butanal | heavy products |
| 17 | A | 14.6 | 76.0 | 6.0 | 3.5 | 14.5 |
| 18 | SAP 350 | 1.70 | 65.0 | 35.0 | — | — |
| 19 | BAE 52A | 3.70 | 78.0 | 14.5 | — | 7.5 |
| 20 | GBS | 14.5 | 82.0 | 2.5 | 1.5 | 14.0 |
| 21 | SCS 9 | 2.4 | 48.0 | 52.0 | — | — |

This comparative study shows that the aluminas GBS and A are the most suitable supports for the transformation of crotonaldehyde into thiophene.

EXAMPLES 22 AND 23

Study of the stability of the catalysts.

Tests as regards the production of thiophene were carried out at 400° C. with an $H_2S$/crotonaldehyde ratio of 5 and a contact time of 0.75 second. These tests were carried out firstly on alumina GBS to which 7.0% of $K_2O$ was added, and on alumina A with 7.7% of $K_2O$, that is to say, on the catalyst systems which have given the best results in the previous tests.

The results which are obtained after different operational times of the catalyst are set out below.

| (Example 22) | | | | | |
|---|---|---|---|---|---|
| Hours | Total activity (GBS) | Selectivities % | | | |
| | | Thiophene | light products | butanal | heavy products |
| 20 | 21.5 | 75.0 | 2.0 | 3.0 | 20.0 |
| 40 | 13.4 | 82.0 | 2.8 | 1.7 | 13.5 |
| 60 | 11.3 | 83.0 | 3.9 | 1.1 | 12.0 |
| 80 | 9.8 | 84.0 | 4.6 | 0 | 11.5 |

| (Example 23) | | | | | |
|---|---|---|---|---|---|
| Hours | Total activity (A) | Selectivities % | | | |
| | | Thiophene | light products | butanal | heavy products |
| 20 | 20.2 | 81.0 | 2.2 | 2.3 | 14.5 |
| 40 | 16.8 | 88.0 | 1.3 | 1.2 | 9.5 |
| 60 | 15.2 | 88.5 | 1.5 | 1.5 | 7.5 |
| 80 | 13.7 | 88.5 | 1.6 | — | 7.5 |
| 100 | 12.8 | 88.0 | 1.7 | — | 8.0 |
| 120 | 11.1 | 86.5 | 2.6 | — | 8.0 |
| 140 | 10.1 | 85.7 | 4.5 | — | 6.6 |

It is seen that the two catalysts which have been tested have activities which are quite comparable as a function of time. After having operated for about 20 hours, the deactivation is then relatively slow and regular as a function of time; it is in fact about 0.12% per hour; the selectivity of thiophene is always high, being of the order of 85%.

The light secondary products, formed of $C_3$ hydrocarbons, particularly propene, and $C_4$ hydrocarbons, mainly butadiene, can be easily eliminated from the reaction mixture; the separation of the thiophene from this mixture is thus a simple matter.

EXAMPLE 24

Influence of the partial pressures of crotonaldehyde and hydrogen sulphide.

The catalyst is formed by alumina A with 7.7% of $K_2O$; the reaction takes place at 400° C. with a contact time of 0.5 second.

The pressure of crotonaldehyde and the pressure of $H_2S$ are modified from one test to the other. The experiments lasted 70 hours.

The following table gives the results of these tests, for an operating period of 50 hours.

| Partial pressures in atm. | | | |
|---|---|---|---|
| Crotonaldehyde $P_1$ | $H_2S$ $P_2$ | Ratio $P_2/P_1$ | Selectivity % of thiophene |
| 0.0615 | 0.576 | 9.35 | 87.5 |
| 0.1150 | 0.576 | 5 | 78.5 |
| 0.1885 | 0.576 | 3.05 | 71.7 |
| 0.115 | 0.885 | 7.7 | 82.5 |
| 0.115 | 0.576 | 5 | 78.5 |
| 0.115 | 0.346 | 3 | 73.0 |

It is apparent from these values that the selectivity as regards thiophene is assisted by an excess of hydrogen sulphide. The results are better in proportion as the ratio $P_2/P_1$ is higher; the $P_2/P_1$ ratios from 3 to 5, which can be easily obtained in practice, give very satisfactory thiophene selectivity values, generally of the order of 70 to 75%.

EXAMPLE 25

The part played by the temperature and the contact time in an industrial reactor.

Operations for preparing thiophene were carried out, using a molar ratio $H_2S$/crotonaldehyde of 5, on an alumina A catalyst with 7.7% of $K_2O$, in an industrial reactor; the work was carried out with a high rate of conversion of crotonaldehyde with variable contact times and temperatures.

The following results were obtained (t represents the contact time in seconds).

| T° C | t | Conversion % of crotonaldehyde | Selectivity as regards thiophene % | Yield of thiophene % |
|---|---|---|---|---|
| | 3.65 | 42 | 75 | 31 |
| | 6.85 | 64 | 69 | 44 |
| 350° C | 9.10 | 75 | 69 | 52 |
| | 13.70 | 87 | 66 | 58 |
| | 3.65 | 86 | 73 | 63 |
| 370° C | 6.85 | 95 | 69 | 65 |
| | 9.10 | 98 | 67 | 65 |
| | 0.75 | 31 | 87 | 27 |
| 400° C | 1.40 | 52 | 82 | 43 |
| | 3.65 | 99 | 69 | 68 |

It is seen that the results obtained kinetically are correctly transposed to the industrial reactor; the preparation of thiophene in accordance with the invention may thus be carried into effect with good yields.

EXAMPLES 26 TO 32

In this series of examples, starting with different initial carbonyl derivatives, unsubstituted thiophene (Example 26) and substituted thiophenes (Examples 27 to 32) were prepared, in which the positions of the substituents are represented by the following numbering:

The reaction was carried out at 400° C. on an alumina A catalyst containing 7.7% of K₂O. The ratio between the partial pressures of the H₂S and those of the initial carbonyl compound were fixed at a value of 5.

The results are set out in the table which is given below; the contact times of the reaction medium with the catalyst are given by the equivalent value of m/F, in which m is the weight of catalyst in grams and F is the rate of flow of gas in moles per hour.

| Ex. No. | Initial carbonyl compound | Thiophene obtained | m/F | % conversion | % selectivity |
|---|---|---|---|---|---|
| 26 | CH₃CH=CH—CHO crotonaldehyde | thiophene | 3.6 | 35 | 77 |
| 27 | CH₃CH=CH—C(O)—CH₃ 3-pentene-2-one | 2-methyl-thiophene | 7.5 | 50 | 72 |
| 28 | CH₃CH=C(CH₃)—CHO 2-methyl-2-butenal | 3-methyl-thiopene | 7.5 | 52 | 77 |
| 29 | CH₃—C(CH₃)=CH—C(O)—CH₃ 4-methyl-3-pentene-2-one | 2,4-dimethyl-thiopene | 5.0 | 20 | 70 |
| 30 | CH₃CH₂CH=C(CH₃)—CHO 2-methyl-2-pentenal | " | 9.0 | 54 | 67 |
| 31 | CH₃CH₂CH₂CH=CHCHO 2-hexenal | 2-ethyl-thiopene | 8.5 | 55 | 54 |
| 32 | CH₃CH₂CH₂CH=C(CH₂CH₃)—CHO 2-ethyl-2-hexenal | 2,4-diethyl-thiophene | 9.8 | 50 | 60 |

EXAMPLE 33

Under the same conditions as in Examples 26 to 32, the benzo (c) thiophene

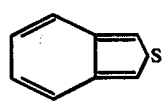

was synthesised from ortho-tolualdehyde. The m/F ratio was 9.1, the conversion of aldehyde was 28% and the selectivity of benzo (c) thiophene was 14%. Although these results are smaller than those of the foregoing examples, they are all of equal interest, because it does not seem to be possible to obtain a benzo (c) thiophene with better yields by a known method.

EXAMPLE 34

Benzo (b) thiophene was prepared by the operating procedure of Example 33, starting with phenyl-acetaldehyde C₆H₅CH₂CHO. The m/F ratio being used was 9.1. The benzo (b) thiophene

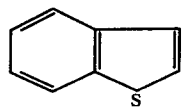

was obtained with a selectivity of 7%, for a conversion of phenyl-acetaldehyde of 40%.

We claim:

1. A method for preparing thiophenes, which comprises reacting in the presence of an alumina catalyst between 250° and 500° C. hydrogen sulfide with a compound selected from the group consisting of the unsaturated carbonyl and thiocarbonyl compounds represented by the formula

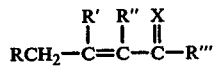

where X is O or S while each of the symbols R, R', R" and R'" is hydrogen or lower alkyl, or ortho-tolualdehyde or phenyl-acetaldehyde, then condensing the reaction mixture and separating the thiophene formed.

2. Method according to claim 1 wherein the reaction is carried out at about 300° C. to about 400° C.

3. Method according to claim 1, wherein the compound selected is crotonaldehyde.

4. Method according to claim 1, wherein the compound selected is mesityl oxide.

5. Method according to claim 1, wherein the compound selected is methylethyl acrolein.

6. Method according to claim 1, wherein the compound selected is 3-penten-2-one.

7. Method according to claim 1, wherein the compound selected is 2-methyl-2-butenal.

8. Method according to claim 1, wherein the compound selected is 2-n.hexenal.

9. Method according to claim 1, wherein the compound selected is 2-ethyl-2-hexenal.

10. Method according to claim 1, wherein the alumina used as catalyst contains γ alumina.

11. Method according to claim 10, wherein the alumina is incorporated with 0.5 to 15% by weight of a compound selected from the group consisting of $Na_2O$, $K_2O$, $Na_2S$ and $K_2S$.

12. Method according to claim 11, in which the catalyst has a specific area in the range of about 60 to about 350 $m^2/g$.

13. Method according to claim 12, in which the reaction is carried out under a pressure of 1 to 10 bars.

14. Method according to claim 1, wherein the amount of hydrogen sulfide is about 2 to about 5 moles per mole of said selected compound.

15. Method according to claim 11, wherein the amount of hydrogen sulfide is about 2 to about 5 moles per mole of said selected compound.

* * * * *